United States Patent [19]

Holm et al.

[11] 4,073,637

[45] Feb. 14, 1978

[54] CYCLOHEXIMIDE-IMIDE OR CARBAMATE COMBINATIONS AS FRUIT ABSCISSION AGENTS

[75] Inventors: Robert E. Holm; Robert D. Battershell, both of Painesville, Ohio

[73] Assignee: Diamond Shamrock Corporation, Cleveland, Ohio

[21] Appl. No.: 603,289

[22] Filed: Aug. 11, 1975

[51] Int. Cl.² .............................................. A01N 9/22
[52] U.S. Cl. ........................................ 71/94; 71/74; 71/90; 71/95; 71/97
[58] Field of Search ...................................... 71/94, 74

[56] References Cited

U.S. PATENT DOCUMENTS 3,663,199  5/1972  Cooper .................................. 71/94

Primary Examiner—Lewis Gotts
Assistant Examiner—Catherine L. Mills
Attorney, Agent, or Firm—Stuart L. Melton

[57] ABSTRACT

A combination of cycloheximide and certain imides or carbamates is a synergistic composition capable of promoting fruit, especially citrus fruit, abscission when applied to trees bearing same.

3 Claims, No Drawings

CYCLOHEXIMIDE-IMIDE OR CARBAMATE COMBINATIONS AS FRUIT ABSCISSION AGENTS

BACKGROUND OF THE INVENTION

The desirability of facilitating the harvest of various agricultural crops, especially fruit crops such as citrus fruits, is readily apparent. A number of chemical compounds capable of promoting fruit abscission has been proposed, which compounds serve to reduce the pull force necessary to remove mature fruit from the tree or plant, thereby rendering mechanical harvesting possible. Few of these compounds, however, have found practical utility, mainly owing to their tendency to injure immature fruit and cause blossom drop and/or their simultaneous defoliant effect.

One compound currently in use as a citrus fruit abscission agent is cycloheximide, i.e., 3(2-[3,5-dimethyl-2-oxocyclohexyl]-2-hydroxyethyl) glutarimide. This use is described more fully in U.S. Pat. No. 3,663,199. While the compound is indeed effective in reducing the pull force necessary to remove citrus fruit from trees, its use has been seasonally limited on some citrus varieties (e.g., Valencia oranges) since its application in an amount sufficient to cause the desired abscission, can also result in damage to immature fruit and cause leaf and bloom drop.

STATEMENT OF THE INVENTION

Therefore, it is an object of the present invention to provide a composition and method capable of promoting seasonwide abscission of mature fruit, while reducing undesirable side effects.

It is a further object of the present invention of increase the ability of cycloheximide to promote fruit abscission.

These and other objects of the present invention will become apparent to those skilled in the art from the specification and claims that follow.

There has now been found a composition capable of promoting fruit abscission, which composition consists essentially of cycloheximide and a compound from the group N-[(trichloromethyl)thio] phthalimide, N-[(trichloromethyl)thio]-4-cyclohexene-1,2-dicarboximide, cis-N-[(1,1,2,2-tetrachloroethyl)thio]-4-cyclohexene-1,2-dicarboximide, ferric dimethyldithiocarbamate, ethylenebisdithiocarbamate manganese, ethylenebisdithiocarbamate zinc, and methyl-1-(butylcarbamoyl)-2-benzimidazolecarbamate. Application of such a composition to a fruit locus in an abscission-promoting amount reduces the force subsequently required to remove the fruit from the tree.

DESCRIPTION OF THE PREFERRED EMBODIMENTS

Throughout the specification and claims, the term "fruit" is used to define a variety of agricultural products, the removal of which from the parent plant or tree (hereinafter, tree) may be promoted by the use of an abscission agent. Typically included are oranges, lemons, grapefruit, limes, olives, cherries, apples, pecans, and walnuts. Especially important, and referred to particularly hereinafter, are the citrus fruits.

It has been theorized and substantially demonstrated that one abscission mechanism involves the increased production of ethylene within the fruit, which triggers the abscission process. Cycloheximide is a compound which, when applied externally to mature fruit, increases internal ethylene production and, shortly thereafter, reduces the pull force necessary to remove the fruit. A direct correlation has been confirmed between the ability of a compound or composition to stimulate internal fruit ethylene production and its ability to facilitate fruit abscission.

The present invention makes use of the ability of certain imides and carbamates to increase this internal ethylene production, i.e., the amount of ethylene produced per a given quantity of cycloheximide is significantly increased. A reduction in the pull force necessary to cause abscission follows. This is thought to be surprising since the imides and carbamates themselves do not act to produce any significant quantities of ethylene in fruit when externally applied. Thus, the invention allows the use of a lesser quantity of cycloheximide, thereby reducing injury to the tree and any blooms and immature fruit, or causes an increased abscission-promoting effect at the same cycloheximide concentration. While higher amounts have been recommended when applying cycloheximide alone, the present invention demonstrates commercially acceptable results at cycloheximide concentrations in the applied formulation within the range of from 2 to 20 especially 5-15, parts per million.

The compounds capable of synergizing the effect of cycloheximide as a fruit abscission agent are more completely defined as follows:

N-[(trichloromethyl)thio] phthalimide:

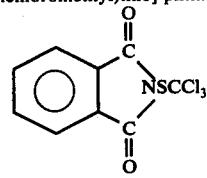

cis-N-[(trichloromethyl)thio]-4-cyclohexene-1,2-dicarboximide:

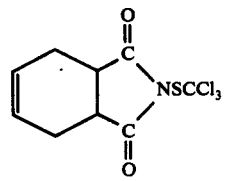

cis-N-[(1,1,2,2-tetrachloroethyl)thiol]-4-cyclohexene-1,2-dicarboximide:

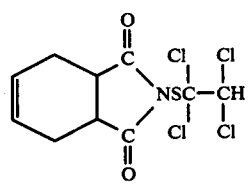

ferric dimethyldithiocarbamate:

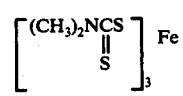

ethylenebisdithiocarbamate manganese:

ethylenebisdithiocarbamate zinc:

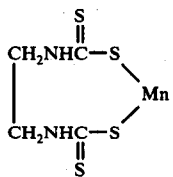

methyl-1-(butylcarbamoyl)-2-benzimidazolecarbamate:

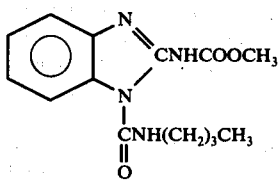

The foregoing compounds are effective when applied to the fruit locus at a total concentration ranging between 50 and 1000 ppm. The ratio of the imide or carbamate to cycloheximide is within the range of from 10 to 200:1, preferably 10 to 50:1, by weight.

The composition will generally be applied as an aqueous spray formulation, this being most convenient and economical, although dusting or other methods of application are possible. Preparation of the aqueous formulation merely requires the dispersion or emulsification of the materials in water at the stated concentration ranges employing a nonphytotoxic surfactant, such as polyoxyethylated sorbitan monolaurate.

Thus, when the fruit has reached substantial maturity, the abscission-promoting composition is applied, generally 5 to 10 days prior to the desired harvesting date, by spraying the fruit locus, although the entire tree may be treated for convenience. Application may be by low volume spray, to run-off, or otherwise as may be desired. Harvesting is then accomplished by exerting sufficient force on the fruit to remove it from the tree. Often, the weight of the fruit alone will cause it to fall from the tree, demonstrating a pull force of less than 0.5 kg. More typically, some positive force must be applied, such as mechanical shaking or from air or water guns.

In order that those skilled in the art may more readily understand the present invention and certain preferred embodiments by which it may be carried into effect, the following specific examples are afforded.

EXAMPLE 1

This example demonstrates the ability of the present invention to increase ethylene production upon external application of the composition to fruit. Acetone solutions of cycloheximide (CHI) and/or the stated compounds are prepared in concentrations such that 1 ml contains the amount of active ingredient(s) set forth in the following Table I. Hamlin oranges are selected for uniformity of size, color, shape, and freedom from imperfections. These oranges are then sprayed with 1 ml of the solution in question, loosely covered with clear plastic, and placed in a growth chamber maintained at 24° C daytime and 16° C nighttime with a light intensity of 800 $\mu E/m^2/sec$. At the indicated intervals a syringe is employed to extract a gas sample from inside the orange near the stem area, which sample is then analyzed for ethylene by gas chromatography on an instrument sensitive to the 10 ppb level. Each result reported is the average of four replicated tests.

TABLE I

| CHI ($\mu$g/fruit) | Compound | ($\mu$g/fruit) | Internal 3 day (ppm/ml) | Ethylene 7 day (ppm/ml) |
|---|---|---|---|---|
| 0 | — | 0 | 0.10 | 0.06 |
| 5 | — | 0 | 0.78 | 0.38 |
| 0 | N-[(trichloromethyl)thio] phthalimide | 50 | 0.13 | 0.07 |
| 0 | " | 250 | 0.15 | 0.14 |
| 5 | " | 50 | 2.11 | 1.74 |
| 5 | " | 250 | 3.61 | 1.44 |
| 0 | cis-N-[(trichloromethyl)thio]-4-cyclo- | 50 | 0.09 | 0.06 |
| 0 | hexene-1,2-dicarboximide | 250 | 0.15 | 0.09 |
| 5 | " | 50 | 1.08 | 0.57 |
| 5 | " | 250 | 2.10 | 0.34 |
| 0 | cis-N-[(1,1,2,2-tetrachloroethyl)thio]- | 50 | 0.10 | 0.10 |
| 0 | 4-cyclohexene-1,2-dicarboximide | 250 | 0.19 | 0.15 |
| 5 | " | 50 | 0.98 | 1.09 |
| 5 | " | 250 | 1.78 | 0.89 |
| 0 | ferric dimethyldithiocarbamate | 50 | 0.11 | 0.07 |
| 0 | " | 250 | 0.16 | 0.28 |
| 5 | " | 50 | 2.01 | 2.01 |
| 5 | " | 250 | 1.80 | 1.21 |
| 0 | ethylenebisdithiocarbamate Mn | 50 | 0.11 | 0.09 |
| 0 | " | 250 | 0.13 | 0.11 |
| 5 | " | 50 | 1.41 | 1.85 |
| 5 | " | 250 | 1.09 | 0.59 |
| 0 | ethylenebisdithiocarbamate Zn | 50 | 0.09 | 0.09 |
| 0 | " | 250 | 0.15 | 0.11 |
| 5 | " | 50 | 1.04 | 0.92 |
| 5 | " | 250 | 1.51 | 1.07 |
| 0 | methyl-1-(butylcarbamoyl)-2- | 50 | 0.11 | 0.11 |
| 0 | benzimidazolecarbamate | 250 | 0.11 | 0.08 |
| 5 | " | 50 | 1.42 | 0.99 |
| 5 | " | 250 | 1.44 | 0.43 |

From Table I the increase in internal ethylene production is readily apparent upon the addition of each compound to the CHI. This occurs even though the imides or carbamates alone have little or no effect on ethylene production. Significantly, the ethylene values often remain at elevated levels for longer periods of time when the combination of ingredients is employed, than when CHI is used alone. This characteristic allows more latitude in harvesting the fruit in the event, for example, of adverse climate conditions.

EXAMPLE 2

In this example the comparative effect of the present invention is evaluated on growing Hamlin oranges. In each instance branches on two separate Hamlin orange trees, each bearing from 20 to 30 mature fruit, are treated to run-off with aqueous solutions or suspensions as indicated in Table II. Each test solution or suspension is prepared using a formulation base consisting of a nonionic surfactant and thickening, anticaking, antifoaming, and freeze-point depressing agents. Seven days after spray application of the abscission agents, the observations appearing in Table II are recorded. Each of the imides and the carbamate tested alone at 50, 100, and 250 ppm, has no measurable effect on fruit abscission. Each test reported in Table II is the average of two replicate treatments.

TABLE II

| CHI (ppm) | Compound | (ppm) | PF[1] | Reduction % | FF[2] |
|---|---|---|---|---|---|
| 0 | formulation base, no active ingredient | 0 | 4.7 | — | 0 |
| 5 | — | 0 | 3.7 | 21 | 1 |
| 5 | N-[(trichloromethyl)thio] phthalimide | 50 | 2.9 | 39 | 1 |
| 5 | " | 100 | 2.0 | 57 | 3 |
| 5 | " | 250 | 1.5 | 69 | 2 |
| 10 | " | 50 | 2.4 | 49 | 8 |
| 10 | " | 100 | 0.9 | 81 | 10 |
| 10 | " | 250 | >0.5 | 100 | 5 |
| 5 | cis-N-[(trichloromethyl)thio]-4-cyclo- | 50 | 3.2 | 33 | 0 |
| 5 | hexene-1,2-dicarboximide | 100 | 3.0 | 36 | 6 |
| 5 | " | 250 | 2.5 | 47 | 5 |
| 10 | " | 50 | 2.7 | 42 | 4 |
| 10 | " | 100 | 2.0 | 57 | 6 |
| 10 | " | 250 | 0.9 | 81 | 10 |
| 5 | cis-N-[(1,1,2,2-tetrachloroethyl)thio]- | 50 | 3.1 | 34 | 0 |
| 5 | 4-cyclohexene-1,2-dicarboximide | 100 | 2.9 | 38 | 0 |
| 5 | " | 250 | 2.7 | 42 | 5 |
| 10 | " | 50 | 2.3 | 52 | 6 |
| 10 | " | 100 | 2.2 | 54 | 2 |
| 10 | " | 250 | 1.9 | 60 | 1 |
| 5 | ethylenebisdithiocarbamate Zn | 50 | 3.5 | 27 | 0 |
| 5 | " | 100 | 3.0 | 36 | 4 |
| 5 | " | 250 | 2.7 | 42 | 0 |
| 10 | " | 50 | 2.8 | 40 | 2 |
| 10 | " | 100 | 2.5 | 46 | 7 |
| 10 | " | 250 | 1.9 | 60 | 10 |

[1]Pull force to remove fruit, in kg.
[2]Mature fruit fall

Table II demonstrates the extent of mature fruit fall and the reduction in pull force on the remaining fruit that is obtainable with the present invention. The table also substantiates the correlation between increased ethylene production, as shown in Table I, and the promotion of fruit abscission.

We claim:

1. A composition capable of promoting fruit abscission, which composition consists essentially of cycloheximide and N-[(trichloromethyl)thio] phthalimide wherein the amount of said cycloheximide in said composition is not in excess of about 20 ppm.

2. A method of harvesting mature fruit from a tree, which method comprises applying to the fruit locus an abscission-promoting amount of a composition consisting essentially of cycloheximide in an amount not in excess of about 20 ppm and N-[(trichloromethyl)thio] phthalimide and subsequently exerting sufficient force on said fruit to remove same.

3. The composition as in claim 1 wherein the weight ratio of said phthalimide to cycloheximide is between about 5 to 50:1.

* * * * *